United States Patent [19]
Lampropoulos et al.

[11] Patent Number: 5,163,904
[45] Date of Patent: Nov. 17, 1992

[54] SYRINGE APPARATUS WITH ATTACHED PRESSURE GAUGE

[75] Inventors: Fred P. Lampropoulos; William Padilla, both of Salt Lake City, Utah

[73] Assignee: Merit Medical Systems, Inc., Salt Lake City, Utah

[21] Appl. No.: 790,389

[22] Filed: Nov. 12, 1991

[51] Int. Cl.⁵ .............................................. A61M 29/00
[52] U.S. Cl. ..................................... 604/100; 604/121
[58] Field of Search .................................... 604/96–100, 604/118–121, 152; 606/192–195; 600/18

[56] References Cited

U.S. PATENT DOCUMENTS

| | | | |
|---|---|---|---|
| 383,940 | 6/1888 | Brinkerhoff. | |
| 404,105 | 5/1889 | Overlach. | |
| 446,125 | 2/1891 | Schirmer. | |
| 466,125 | 2/1891 | Schirmer. | |
| 577,682 | 2/1897 | Eissner. | |
| 730,054 | 6/1903 | Sheets. | |
| 1,661,818 | 3/1928 | Cook. | |
| 1,707,880 | 4/1929 | Sheets. | |
| 2,656,836 | 10/1953 | Hickey | 128/218 |
| 2,672,866 | 3/1954 | Kater | 128/218 |
| 2,699,168 | 1/1955 | Lewis | 128/218 |
| 2,724,385 | 11/1955 | Lockhart | 128/261 |
| 2,736,315 | 2/1956 | Feeney | 128/218 |
| 2,764,978 | 10/1956 | Everett | 128/215 |
| 3,080,866 | 3/1963 | Friedman | 128/218 |
| 3,388,941 | 6/1968 | Marcus | 294/4 |
| 3,478,937 | 11/1969 | Solowey | 222/386 |
| 3,491,757 | 1/1970 | Arce | 128/221 |
| 3,529,596 | 9/1970 | Garner | 128/145.6 |
| 3,698,381 | 10/1972 | Federico et al. | 128/1 R |
| 3,720,199 | 3/1973 | Rishton et al. | 128/1 D |
| 3,884,229 | 5/1975 | Raines et al. | 128/221 |
| 3,931,822 | 1/1976 | Marici | 128/351 |
| 3,966,358 | 6/1976 | Heimes et al. | 417/12 |
| 3,985,123 | 10/1976 | Herzlinger et al. | 128/2.05 F |
| 3,992,926 | 11/1976 | Berryhill | 73/80 |
| 4,016,871 | 4/1977 | Schiff | 128/2.6 R |
| 4,057,050 | 11/1977 | Sarstedt | 128/2 F |
| 4,063,662 | 12/1977 | Drummond et al. | 222/31 |
| 4,086,653 | 4/1978 | Gernes | 364/564 |
| 4,106,002 | 8/1978 | Hogue, Jr. | 340/626 |
| 4,182,344 | 2/1980 | Benson | 128/207.15 |
| 4,231,715 | 11/1980 | Gleichner | 604/121 X |
| 4,254,773 | 3/1981 | Waldbillig | 128/348 |
| 4,266,550 | 5/1981 | Bruner | 128/349 |

(List continued on next page.)

FOREIGN PATENT DOCUMENTS

| | | |
|---|---|---|
| 545415 | 8/1957 | Canada. |
| 0119296 | 9/1984 | European Pat. Off.. |
| 1242737 | 8/1960 | France. |
| 2083364A | 3/1982 | United Kingdom. |

OTHER PUBLICATIONS

"ACS Accessories Offer Optimum Efficiency in Your Angioplasty Procedures," Eli Lilly and Company, undated.

Advertising brochure of North American Instrument Corporation entitled "The NAMIC 10cc Angiographic Syringe Features," undated.

Advertising brochure of Spectramed, Inc.; product
(List continued on next page.)

*Primary Examiner*—John D. Yasko
*Assistant Examiner*—Adam J. Cermak
*Attorney, Agent, or Firm*—Workman Nydegger Jensen

[57] ABSTRACT

A syringe apparatus is described which has a novel adaptor assembly used for mounting a strain gauge to the syringe barrel. The adaptor assembly includes a housing in the form of a well formed on the distal end of the syringe barrel, and a housing insert which fits into the well and which caps the well when fully inserted. The housing insert in turn receives the mounting post of a strain gauge without having to thread the mounting post of the strain gauge into the housing insert. The housing insert properly aligns the mounting post of the strain gauge with an opening in the syringe barrel that provides fluid communication for purposes of reading pressures in the syringe barrel, and also properly rotationally orients the strain gauge so that the dial of the strain gauge is readable from the proximal end of the syringe apparatus.

9 Claims, 3 Drawing Sheets

U.S. PATENT DOCUMENTS

| | | | |
|---|---|---|---|
| 4,267,846 | 5/1981 | Kontos | 128/765 |
| 4,285,340 | 8/1981 | Gezari et al. | 128/205.24 |
| 4,323,071 | 4/1982 | Simpson et al. | 128/343 |
| 4,332,254 | 6/1982 | Lundquist | 128/344 |
| 4,370,982 | 2/1983 | Reilly | 604/98 |
| 4,384,470 | 5/1983 | Fiore | 73/4 R |
| 4,392,847 | 7/1983 | Whitney et al. | 604/118 |
| 4,404,974 | 9/1983 | Titus | 128/670 |
| 4,418,392 | 11/1983 | Hata | 364/571 |
| 4,439,185 | 3/1984 | Lundquist | 604/97 |
| 4,444,335 | 4/1984 | Wood et al. | 222/43 |
| 4,446,715 | 5/1984 | Bailey | 73/1 R |
| 4,446,867 | 5/1984 | Leveen et al. | 128/344 |
| 4,466,426 | 8/1984 | Blackman | 128/1.1 |
| 4,504,268 | 3/1985 | Herlitze | |
| 4,522,194 | 6/1985 | Normann | 128/1 D |
| 4,526,196 | 7/1985 | Pistillo | 137/557 |
| 4,546,760 | 10/1985 | Suzuki et al. | 128/1 D |
| 4,557,269 | 12/1985 | Reynolds et al. | 128/675 |
| 4,568,335 | 2/1986 | Updike et al. | 604/211 |
| 4,573,978 | 3/1986 | Reilly | 604/240 |
| 4,583,917 | 4/1986 | Shah | 417/63 |
| 4,583,974 | 4/1986 | Kokernak | 604/211 |
| 4,585,010 | 4/1986 | Ascer et al. | 128/673 |
| 4,596,255 | 6/1986 | Snell et al. | 128/697 |
| 4,597,381 | 7/1986 | Oumi et al. | 128/6 |
| 4,600,015 | 7/1986 | Evans et al. | 128/780 |
| 4,601,701 | 7/1986 | Mueller, Jr. | 604/83 |
| 4,610,256 | 9/1986 | Wallace | 128/675 |
| 4,621,646 | 11/1986 | Bryant | 128/692 |
| 4,651,783 | 3/1987 | Demer et al. | 128/344 |
| 4,654,027 | 3/1987 | Dragon et al. | 604/99 |
| 4,655,749 | 4/1987 | Fischione | 604/98 |
| 4,672,974 | 6/1987 | Lee | 128/673 |
| 4,710,179 | 12/1987 | Haber | 604/211 |
| 4,715,854 | 12/1987 | Vaillancourt | 604/191 |
| 4,723,938 | 2/1988 | Goodin et al. | 604/99 |
| 4,743,230 | 5/1988 | Nordquest | 604/97 |
| 4,758,223 | 7/1988 | Rydell | 604/90 |
| 4,781,192 | 11/1988 | Demer | 128/344 |
| 4,787,368 | 11/1988 | Kageyama | 600/18 |
| 4,787,429 | 11/1988 | Valentini et al. | 141/383 |
| 4,790,821 | 12/1988 | Stines | 604/98 |
| 4,796,606 | 1/1989 | Mushika | 600/18 |
| 4,799,491 | 1/1989 | Eckerle | 128/672 |
| 4,819,637 | 4/1989 | Dormandy, Jr. et al. | 128/325 |
| 4,820,271 | 4/1989 | Deutsch | 604/99 |
| 4,825,876 | 5/1989 | Beard | 128/675 |
| 4,830,013 | 5/1989 | Maxwell | 128/637 |
| 4,832,692 | 5/1989 | Box et al. | 604/99 |
| 4,838,684 | 6/1989 | Peterson | 604/100 |
| 4,858,615 | 8/1989 | Meinema | 128/668 |
| 4,872,483 | 10/1989 | Shah | 137/557 |
| 4,877,035 | 10/1989 | Bogen et al. | 128/673 |
| 4,896,671 | 1/1990 | Cunningham et al. | 128/642 |
| 4,901,731 | 2/1990 | Millar | 128/675 |
| 4,906,244 | 3/1990 | Pinchuk et al. | 606/194 |
| 4,907,596 | 3/1990 | Schmid et al. | 128/672 |
| 4,919,121 | 4/1990 | Rydell et al. | 604/97 |
| 4,940,459 | 7/1990 | Noce | 604/97 |
| 4,974,774 | 12/1990 | Nakagawa et al. | 600/18 |
| 5,009,662 | 4/1991 | Wallace et al. | 606/192 |
| 5,019,041 | 5/1991 | Robinson et al. | 604/97 |
| 5,047,015 | 9/1991 | Foote et al. | 604/99 |
| 5,057,078 | 10/1991 | Foote et al. | 604/99 |

OTHER PUBLICATIONS brochure for "Controlease Disposable Control Syringe"; and product brochure for control syringe of Coeur Laboratories, Inc. undated.

"Clearing the Path for a Healthy Heart," *Tristate: The Cincinnati Enquirier Magazine,* Oct. 23, 1988.

"Coronary Angioplasty," Krames Communications, 1985.

"Good News for People with Only Two Hands," SciMed Life Systems, Inc.

"Health—Critics of Angioplasty Worry About Inflated Success Claims," *U.S. News & World Report,* Jul. 25, 1988, p. 65.

"Inflation PRO: A New Dual-Support System for Angioplasty," Baxter Healthcare Corporation, undated.

"PTCA Safe and Efficacious Performed Together With Diagnostic Angiography in Selected Cases," *Cardiovascular News,* May 1988, p. 8.

"USCI Wizard Disposable Inflation Device," C. R. Bard, Inc., 1987.

SYRINGE APPARATUS WITH ATTACHED PRESSURE GAUGE

BACKGROUND

1. Field of the Invention

The present invention relates to the syringe devices, and more particular, to a syringe apparatus to which a pressure gauge is mounted for purposes of reading fluid pressures exerted within the barrel of the syringe.

2. The Prior Art

Syringes are used for many different kinds of medical applications. For example, when performing a coronary angioplasty a syringe apparatus is used to control injection of a contrast media through pressure tubing and through a lumen of a catheter to the distal end of the catheter where a balloon is inflated while positioned in a coronary artery in order to remove coronary artery blockage. Under these circumstances, the syringe must be capable of carefully controlling the injection of the contrast media under high pressures for carefully controlled durations of time. Accordingly, syringes have been devised which are equipped with a pressure gauge that is designed to monitor the pressure being exerted by the syringe on the contrast media as it is injected into the balloon that is located at the distal end of the catheter.

One of the most widely used types of pressure gauges used for this purpose is a simple standard strain gauge which is mounted on the barrel of the syringe. The strain gauge has a dial on the upper face of the gauge and a needle which is used to read pressures within a selected range. Commonly, the strain gauge is mounted to the syringe by the use of a threaded coupling. In other words, typically the syringe barrel is provided with a female threaded fitting and at the base of the strain gauge there is a corresponding threaded male fitting so that the strain gauge can be simply screwed into the female fitting to accomplish the desired attachment.

It is also customary in the art to construct the syringe apparatus from plastic materials in order to reduce the cost of the apparatus, thereby rendering the entire syringe apparatus disposable after a single procedure. On the other hand, the strain gauge device is typically a metal device and the threaded male coupling is most often fabricated from a machined brass part. On the one hand, in view of the relatively high pressures which are required to be exerted by the syringe on the contrast media, the strain gauge must be screwed into the syringe barrel tight enough to prevent leakage from occurring as the syringe is operated. On the other hand, because the female fitting on the syringe barrel is customarily plastic and the male coupling on the strain gauge is brass, screwing the strain gauge too tightly can result in cracking and breaking the female fitting. Accordingly, care must be taken in the assembly of this type of syringe apparatus not to overtighten the threaded coupling.

Another problem which is encountered when attempting to attach the strain gauge using a threaded coupling in the mentioned manner, is that it is difficult to accurately position the dial of the strain gauge while at the same time tightening the strain gauge to the necessary degree without cracking the female coupling. Since typically the dial of the strain gauge must be oriented in a manner so that it can be read from a user who is grasping the syringe plunger at the proximal end of the syringe apparatus, the dial must therefore face the proximal end of the syringe apparatus so that it is readable by the user. This requirement further complicates the difficulty of properly orienting the dial when screwing the strain gauge onto the barrel of the syringe.

BRIEF SUMMARY AND OBJECTS OF THE INVENTION

In view of the prior state of the art, it is a primary object of the present invention to provide a syringe apparatus with an attached pressure gauge wherein the pressure gauge can be quickly and easily mounted to the barrel of the syringe apparatus without the use of a threaded coupling so as to eliminate the problems attendant with overtightening the threaded coupling and cracking the syringe apparatus, while at the same time properly orienting the dial of the strain gauge so that it is readable from the proximal end of the syringe apparatus.

In accordance with the primary object of the invention, it is a further object to provide a syringe apparatus which is designed with an adaptor for attachment of a conventional strain gauge wherein the adaptor accommodates insertion of the strain gauge without a threaded coupling and yet provides for a secure bonding of the strain gauge to the syringe barrel.

Yet a further related object of the present invention is to provide a syringe apparatus which has an adaptor for mounting a strain gauge and wherein the adaptor is designed so that the strain gauge will be correctly oriented such that the dial of the strain gauge is easily readable from the proximal end of the syringe apparatus once the adaptor is mounted onto the syringe barrel with the strain gauge.

The foregoing and other objects of the invention are realized in a syringe apparatus which, briefly summarized, is comprised of a housing that is molded as an integral part of the syringe barrel at the distal end of the syringe barrel. The housing is in the form of a well and an opening is formed at the bottom of the well in order to provide fluid communication with the fluid that is expelled under pressure from the syringe barrel as the plunger is pushed through the barrel. The syringe apparatus also is comprised of a housing insert which fits into the housing well and which also caps the well. The housing insert is designed to receive a mounting post at the base of the strain gauge by means of a sliding fit. The mounting post is bonded into the housing insert so that there is no need for screwing the two together. The housing insert is also designed to automatically correctly orient the strain gauge and also the strain gauge and housing insert assembly as the assembly is mounted onto the housing well formed on the distal end of the syringe barrel.

BRIEF DESCRIPTION OF THE DRAWINGS

The foregoing and other objects and advantages of the invention will be better understood in reference to the drawings and accompanying description, or from the practice of the invention as set forth in the appended claims. Reference is next made to a brief description of the drawings, which are intended to illustrate the present invention with respect to the manner of making and using the same in its presently understood best mode. The drawings and detailed description which follow are intended to be merely illustrative and not otherwise limiting of the scope of the invention as set forth in the appended claims. Included within the drawings are the following figures.

DETAILED DESCRIPTION OF THE PRESENTLY PREFERRED EMBODIMENT OF THE INVENTION

Figure 1:
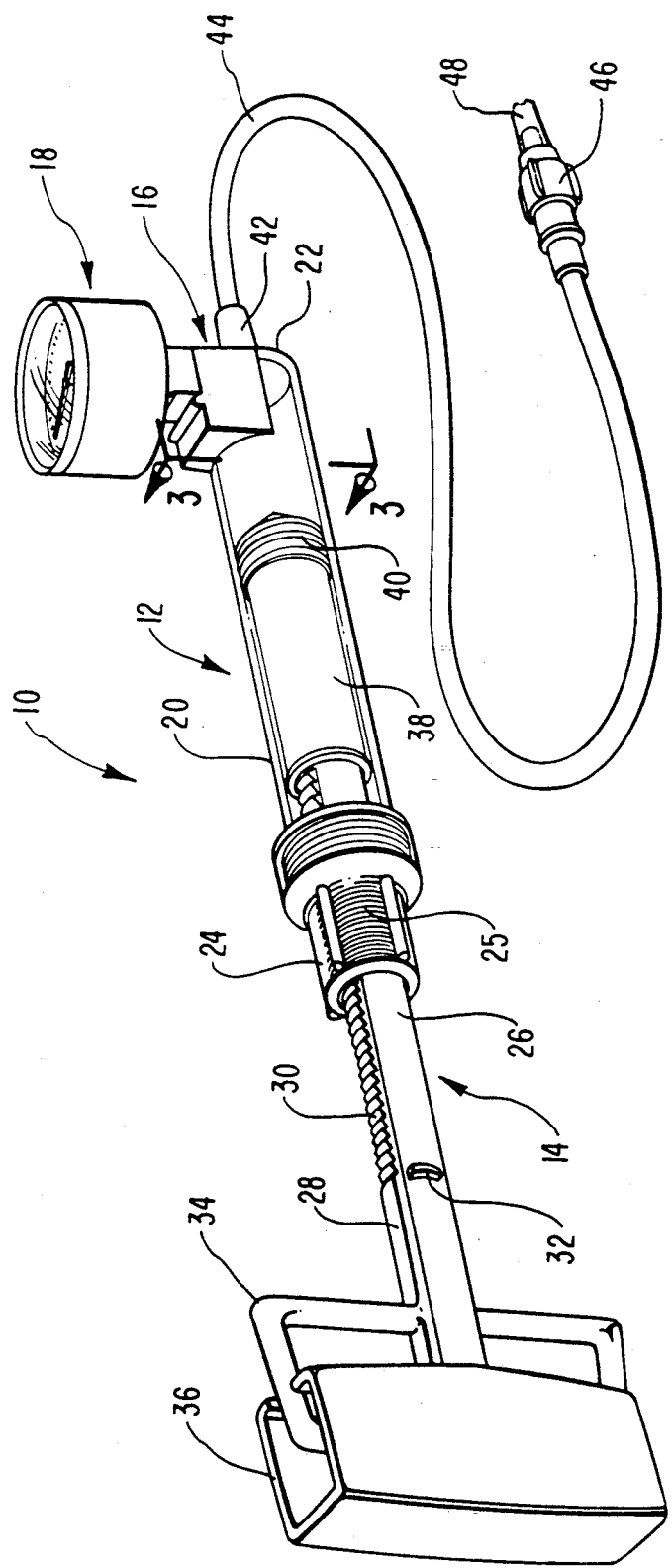
FIG. 1 is a perspective view of one presently preferred embodiment of the invention.

Reference is first made to FIG. 1. The overall syringe apparatus is generally designated at reference numeral 10, and is comprised of a syringe barrel generally designated at 12 and a syringe plunger generally designated at 14. The elongated cylindrical barrel 20 of the syringe apparatus is preferably constructed of a clear polycarbonate, medical grade plastic material which is molded in accordance with conventional molding technology well known in the art. The syringe barrel 20 is comprised of a distal end 22 and a proximal end 24. The proximal end 24 forms a plunger opening which has internal threads 25.

The syringe plunger 14 is comprised of an elongated member 26 which has an upper surface 28 with threads 30 formed on the upper surface 28. The elongated plunger member 26 extends through the plunger opening formed at the proximal end 24 of the barrel 20 so that the distal end of the elongated member 26 is slidably operative through the barrel 20. At the distal end of the elongated plunger member 26 there is a collar 38 which has a rubber tip 40 which provides a fluid-tight seal about the periphery of the barrel so that fluid can be expelled from the syringe barrel 20 as the plunger 14 is pushed further into the barrel 20.

The proximal end of the syringe plunger 14 is comprised of a handle 36 and a trigger mechanism 34. As the trigger mechanism 34 is compressed into the handle 36 the threads 30 on the upper surface 28 are retracted so as to disengage from the internal threads 25 located at the proximal end 24 of the syringe barrel. When the threads 30 are disengaged in this fashion, the elongated plunger member 26 is free to slide in or out of the barrel by pushing or pulling the same. On the other hand, when the trigger mechanism 34 is released, the threads 30 on upper surface 28 will engage the internal threads 25 thereby requiring that the elongated plunger member 26 be screwed in order to advance or retract the plunger into or out of the barrel 20. In this manner, fluid pressures can be quickly exerted and/or released as desired as well as providing for the attainment of very precise pressures by slowly screwing the plunger 14 into or out of the barrel 20.

Preferably, the plunger 14 is also constructed of medical grade plastic material, though typically of an opaque nature. It will appreciated and understood that the nature and mechanical aspects of the syringe are not limited to those which are illustrated in FIG. 1, and a variety of different types of syringe designs could be used without departing from the spirit and scope of the invention as hereinafter more fully described and claimed. The particular syringe apparatus as illustrated in FIG. 1 is more particularly described in U.S Pat. Nos 5,047,015 and 5,057,078, incorporated herein by reference, which further describe, for example, the stop member 32 on the syringe plunger 14.

With continued reference to FIG. 1, at the distal end 22 of syringe barrel 20, there is an adaptor means for mounting the pressure gauge to the distal end of the barrel. As hereinafter more fully described, the adaptor means is comprised of a means for slidably receiving a mounting post of the strain gauge and for aligning the mounting post with an opening formed in the syringe barrel while at the same time rotationally orienting the dial of the gauge as the mounting post of the gauge is fully inserted into the adaptor so that the dial is readable from the proximal end of the barrel. The adaptor means and the manner by which the strain gauge is assembled onto the distal end of the barrel using the adaptor means is more particularly illustrated in FIGS. 2 and 3, to which reference is next made.

Figure 2:
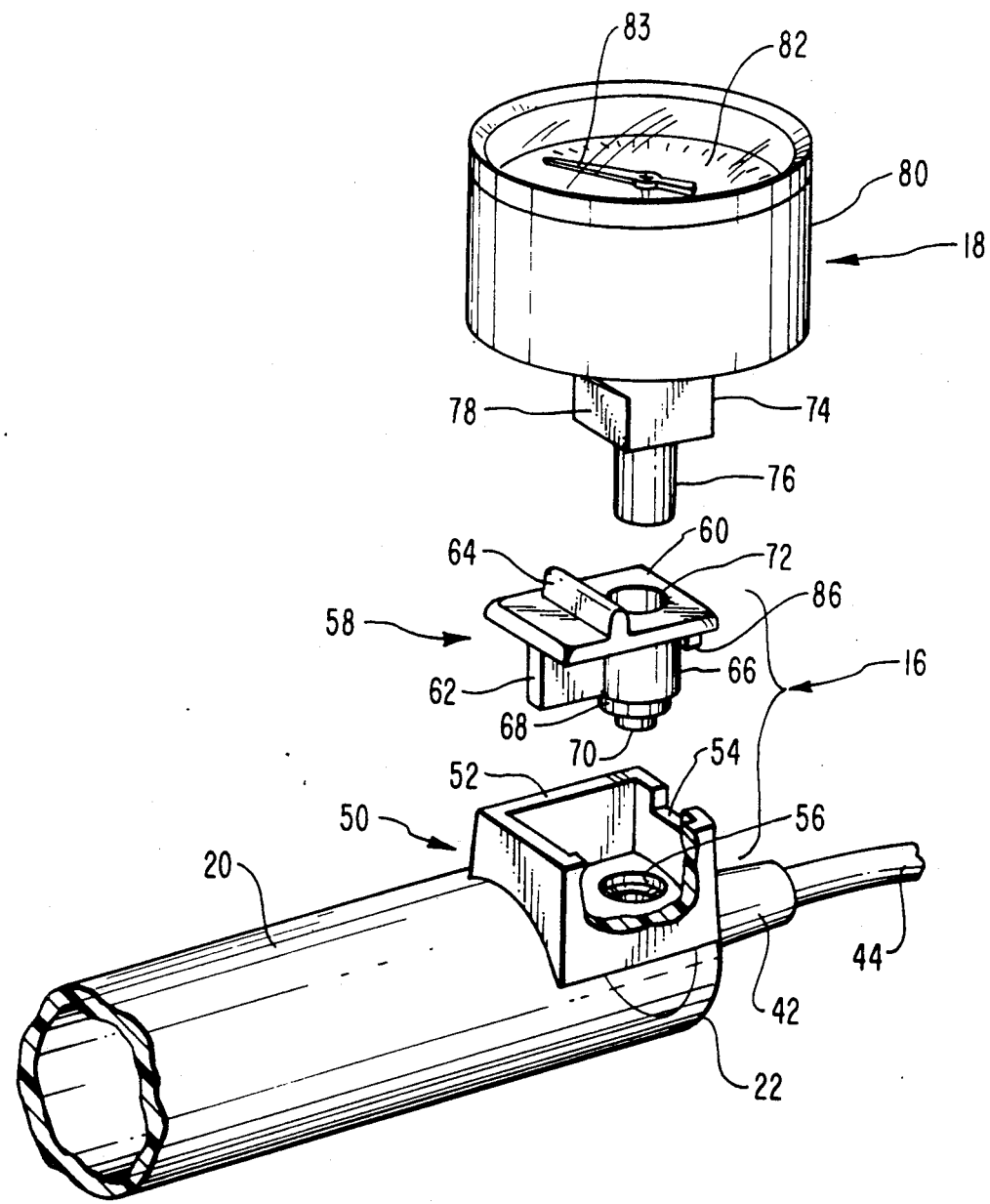
FIG. 2 is an enlarged, exploded perspective view showing the distal end of the syringe barrel together with the housing well formed on the distal end of the syringe barrel, the housing insert and the strain gauge and the manner of assembling those components.

As shown in FIG. 2, in the presently preferred embodiment of the invention the adaptor means is generally illustrated at reference numeral 16, and is comprised of an insert means generally designated at 58 and a housing means generally designated at 50. In the presently preferred embodiment, the housing means 50 is formed as a generally square shaped well which is molded as an integral part on the distal end 22 of the syringe barrel 20. As shown best in FIG. 3, the distal end of the syringe barrel is comprised of two openings which are formed therein. The first opening 57 is located at the end of the syringe barrel and communicates by means of the fitting 42 with pressure tubing 44 that is anchored within the fitting 42. The pressure tubing 44, as shown in FIG. 1, is in turn connected by means of a luer connector 46 to a catheter 48 that is inserted into a patient, as for example in the case of an angioplasty procedure where the tip of the catheter (not shown) includes an inflatable balloon that is to be located within a coronary artery for purposes of inflation in order to remove coronary artery blockage.

The second opening which is formed at the distal end 22 of the barrel 20 is shown best in FIG. 2 at reference numeral 56. The second opening 56 is located at the bottom of the housing well 52 and communicates with the interior of the barrel 20.

The insert means 58 which is adapted for insertion into the well 52 serves as a means for receiving the strain gauge and for mounting the strain gauge onto the housing well 52 so that the housing well 52 is capped and sealed while at the same time properly orienting the dial of the strain gauge so that it is readable from the proximal end of the syringe barrel, and also serves as a means for also aligning the strain gauge with the second opening 56 to permit reading of the fluid pressures within the syringe barrel.

As shown in FIG. 2, the insert means in its presently preferred embodiment is comprised of a generally flat upper surface 60 which fits onto and covers the top of the housing well 52. Extending from the underside of the flat surface 60 is a support rib 62 which, as shown best in FIG. 3, extends to the bottom of the housing well 52 so as to firmly support the upper surface 60. Also extending downwardly from the underside of the upper surface 60 is a cylindrical member 66 which has a corresponding cylindrical bore 72 formed through the interior thereof. The cylindrical member 66 has two diametrally reduced portions 68 and 70 which extend in a telescoping fashion from the bottom of the cylindrical member 66. In a corresponding fashion, the bore of cylindrical member 66 has correspondingly diametrally reduced portions 90 and 92. As will be best appreciated by reference to FIG. 3, the diametrally reduced, telescopically extending portions 68 and 70 fit within correspondingly shaped portions of the opening 56. Thus, as the insert means 58 is inserted into the housing well 52 the cylindrical member 66 will be precisely aligned with the opening 56 that is formed at the upper distal end 22 of syringe barrel 20.

As further best illustrated in FIG. 2, a keyway 54 is provided in the form of a notched portion in one of the sides of the housing well 52. A corresponding key 86 is formed on the underside of the upper flat surface 60 of insert member 58 so that as the insert member 58 is inserted into the housing well 52, the keyway 54 and key 86 will ensure proper orientation of the insert member 58 within housing well 52.

The strain gauge generally designated 18 is a conventional strain gauge which has a dial 82 with a needle 83 that reads pressures. The strain gauge is formed as a rounded housing 80 and at the bottom of the housing 80 there is a mounting block 74 which has at least one flat surface 78. Also, extending from the base of the mounting block 74 there is a mounting post 76. Importantly, the mounting post 76 has a smooth exterior and is not threaded. A cylindrical bore 88, shown in FIG. 3, extends through the center of the mounting post 76 so as to provide communication with the fluid pressures through the opening 56 inside of the syringe barrel 20.

Figure 3:
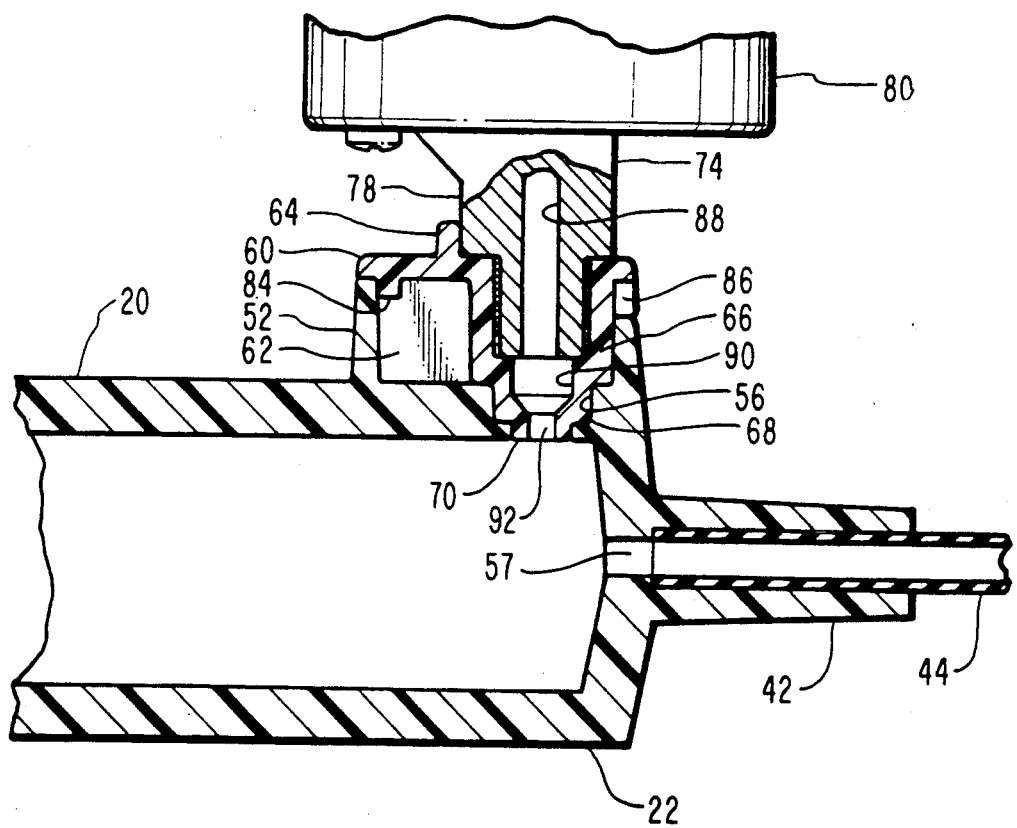
FIG. 3 is an enlarged cross-sectional view of the distal end of the syringe barrel taken along lines 3—3 of FIG. 1, and particularly illustrating the housing insert and strain gauge assembled and mounted within the housing well located at the distal end of the syringe barrel.

As shown best in FIG. 3, as the mounting post 76 is fully inserted into the bore 72 of cylindrical member 66 on the insert means 58, the flat surface 78 abuts against an elongated ridge 64 which is formed on the upper side of the surface 60. The elongated ridge 64 in combination with the flat surface 78 prevent rotation of the strain gauge 80 from occurring the mounting post 76 is fully inserted into the cylindrical member 66. The mounting post 76 is bonded by a resin material within the cylindrical member 66 in order to seal the strain gauge in the housing insert or housing means 58, which is then fully inserted into the housing well 52 and bonded into place with the key 86 fitting into keyway 54, and the diametrally reduced telescopic ends 68 and 70 fitting into the correspondingly shaped opening 56. In this manner, the strain gauge is properly aligned with the opening 56 in the distal end 22 of barrel 20 while at the same time being properly rotationally oriented so that the dial 82 of the strain gauge is readable from the proximal end of the syringe.

As shown best in FIG. 3, a ridge 84 also helps to securely hold the upper surface 60 in abutment with the sides of the housing well 52 and the entire housing insert is securely bonded or otherwise welded so as to form a fluid-tight seal.

As will be appreciated from the foregoing, the strain gauge 18 can be easily and quickly mounted to the syringe barrel without having to utilize any form of threaded coupling thereby eliminating the risk of cracking the plastic parts and also providing an easier assembly method which assures that the dial of the strain gauge is properly rotationally oriented. The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of the equivalency of the claims are to be embraced within their scope.

What is claimed is:

1. A syringe apparatus comprising:
   an elongated cylindrical barrel comprised of a distal end and a proximal end, the distal end comprising first and second openings and a connector means for attachment to tubing, said connector means aligned with said first opening and for providing fluid communication between said tubing and said barrel, and the proximal end comprising a plunger opening;
   an elongated cylindrical plunger slidably mounted through said plunger opening and slidably operative through said barrel to pressurize and expel fluid contained in the barrel through said connector means and tubing;
   pressure gauge means for measuring the pressure exerted on said fluid as it is expelled from said barrel by the plunger, said pressure gauge means comprising a dial and a cylindrical mounting post with a bore therein and said mounting post having a smooth exterior; and
   adaptor means for mounting said pressure gauge means to the distal end of said barrel, said adaptor means comprising means for slidably receiving said mounting post and for aligning the bore of said mounting post with the second opening while at the same time rotationally orienting the dial of said gauge means once the mounting post is fully inserted into the slidable receiving means so that the dial is readable from the proximal end of said barrel.

2. A syringe apparatus as defined in claim 1 wherein said barrel, said plunger and said adaptor means are each constructed of medical grade plastic material.

3. A syringe apparatus as defined in claim 2 wherein said adaptor means comprises:
   a housing molded as an integral part on the distal end of said barrel, said housing forming a well and having said second opening positioned at the bottom of said well; and
   an insert means for insertion into said well and for capping said well.

4. A syringe apparatus as defined in claim 2 wherein said insert means comprises a cylindrical member having a cylindrical bore therethrough, said bore slidably receiving the mounting post of said gauge means, the cylindrical member and the bore of said cylindrical member both being diametrally reduced so as to limit insertion of said mounting post to a selected depth of the bore, and the diametrally reduced portion of the cylindrical member telescopically fitting into said second opening so as to align the second opening with the bore of said cylindrical member and the bore of said mounting post.

5. A syringe apparatus as defined in claim 4 wherein said pressure gauge means comprises a mounting block and wherein said mounting post extends from and is formed as an integral part of said mounting block, said mounting block having one side thereof that is essentially flat, and said insert means comprising an elongated ridge that abuts against said one side of the mounting block that is flat, so as to prevent rotation of the cylindrical member when the mounting post is fully inserted therein.

6. A syringe apparatus as defined in claim 5 wherein a side of said well comprises a keyway and wherein said insert means comprises a key which fits said keyway when the insert means is fully inserted into the well, said keyway and key and said elongated ridge and said one side that is flat together serving to orient the dial of said gauge means so that the dial is readable from the proximal end of said barrel.

7. A syringe apparatus comprising:
  an elongated cylindrical barrel comprised of a distal end and a proximal end, the distal end comprising first and second openings and a connector means for attachment to tubing, said connector means aligned with said first opening and for providing fluid communication between said tubing and said barrel, and the proximal end comprising a plunger opening;
  an elongated cylindrical plunger slidably mounted through said plunger opening and slidably operative through said barrel to pressurize and expel fluid contained in the barrel through said connector means and tubing;
  pressure gauge means for measuring pressure exerted on said fluid as it is expelled from said barrel by the plunger, said pressure gauge means comprising a dial and a mounting block having a cylindrical mounting post attached thereto, said mounting post having a bore therein and having a smooth exterior;
  a housing formed on the distal end of said barrel, said housing forming a well and having said second opening positioned at the bottom of said well and said well having at least one side thereof having a keyway formed therein; and
  an insert means for insertion into said well and for capping said well, said insert means comprising a cylindrical member having a cylindrical bore therethrough, said bore slidably receiving the mounting post of said gauge means, and the cylindrical member and the bore of said cylindrical member both being diametrically reduced so as to limit insertion of said mounting post to a selected depth of the bore, and the diametrally reduced portion of the cylindrical member telescopically fitting into said second opening at the bottom of said well so as to align the second opening with the bore of said cylindrical member and the bore of said mounting post, said insert means further comprising an elongated ridge that abuts against one side of said mounting block to prevent rotation of the mounting block within the cylindrical bore of the cylindrical member when the mounting post is fully inserted therein, and said insert means further comprising a key which fits said keyway formed in the side of said well when the insert means is fully inserted into the well, said keyway and key and said elongated ridge and said mounting block together serving to orient the dial of said gauge means so that the dial is readable from the proximal end of said barrel.

8. A syringe apparatus as defined in claim 7 wherein said barrel, said plunger, said housing and said insert means are each constructed of medical grade plastic material.

9. A syringe apparatus as defined in claim 8 wherein said housing is molded as an integral part of said syringe barrel and wherein said insert means is bonded to said housing by a resin material and wherein the mounting post of said gauge means is bonded to said insert means by a resin material.

* * * * *

UNITED STATES PATENT AND TRADEMARK OFFICE
CERTIFICATE OF CORRECTION

PATENT NO. : 5,163,904

DATED : NOVEMBER 17, 1992

INVENTOR(S) : FRED P. LAMPROPOULOS et al.

It is certified that error appears in the above-identified patent and that said Letters Patent is hereby corrected as shown below:

Column 1, line 65, after "coupling" insert --.--

Column 5, line 39, after "occurring" insert --once--

Signed and Sealed this

Ninth Day of November, 1993

Attest:

BRUCE LEHMAN

*Attesting Officer*　　　*Commissioner of Patents and Trademarks*